United States Patent
Cooper

(10) Patent No.: US 9,520,617 B2
(45) Date of Patent: Dec. 13, 2016

(54) SULFOLANE MIXTURES AS AMBIENT APROTIC POLAR SOLVENTS

(71) Applicant: ADVANCED TECHNOLOGY MATERIALS, INC, Danbury, CT (US)

(72) Inventor: Emanuel I. Cooper, Scarsdale, NY (US)

(73) Assignee: ADVANCED TECHNOLOGY MATERIALS, INC., Danbury, CT (US)

( * ) Notice: Subject to any disclaimer, the term of this patent is extended or adjusted under 35 U.S.C. 154(b) by 0 days.

(21) Appl. No.: 14/211,528

(22) Filed: Mar. 14, 2014

(65) Prior Publication Data

US 2014/0319423 A1 Oct. 30, 2014

Related U.S. Application Data

(60) Provisional application No. 61/781,820, filed on Mar. 14, 2013.

(51) Int. Cl.
*H01M 10/0569* (2010.01)
*C07D 333/48* (2006.01)
*H01M 10/052* (2010.01)

(52) U.S. Cl.
CPC ........ *H01M 10/0569* (2013.01); *C07D 333/48* (2013.01); *H01M 10/052* (2013.01)

(58) Field of Classification Search
CPC ................................................ H01M 10/0569
USPC ....................................................... 252/364
See application file for complete search history.

(56) References Cited

U.S. PATENT DOCUMENTS

| 2,360,589 | A | | 10/1944 | Evans et al. | |
|---|---|---|---|---|---|
| 3,466,346 | A | * | 9/1969 | Perga et al. | 203/58 |
| 3,723,256 | A | * | 3/1973 | Thompson | 3/43 |
| 3,723,484 | A | * | 3/1973 | Laurent et al. | 552/588 |
| 4,024,028 | A | * | 5/1977 | Haskell | 203/51 |
| 4,053,369 | A | * | 10/1977 | Cines | 203/52 |
| 4,363,704 | A | * | 12/1982 | Berg | 203/58 |
| 4,401,517 | A | * | 8/1983 | Lee | 203/53 |
| 5,032,232 | A | * | 7/1991 | Lee et al. | 203/51 |
| 5,849,982 | A | * | 12/1998 | Lee et al. | 585/833 |
| 6,555,726 | B1 | * | 4/2003 | McKim et al. | 585/857 |
| 6,660,899 | B2 | * | 12/2003 | McKim et al. | 585/856 |
| 2003/0042125 | A1 | | 3/2003 | Lee | |
| 2013/0102774 | A1 | | 4/2013 | Pettersson et al. | |
| 2014/0319423 | A1 | * | 10/2014 | Cooper | 252/364 |

FOREIGN PATENT DOCUMENTS

EP 2 484 655 A1 8/2012

OTHER PUBLICATIONS

Extended European Search Report dated May 22, 2014.
Lee, Seung-Yul, et al.; "Lithium Salt Solutions in Mixed Sulfone and Sulfone-Carbonate Solvents: A Walden Plot Analysis of the Maximally Conductive Compositions," The Journal of Physical Chemistry, 2012, 23915-23920, vol. 116.
Tilstam, Ulf, "Sulfolane: A Versatile Dipolar Aprotic Solvent," Organic Process Research & Development, 2012, 1273-1278, vol. 16.
Martinmaa, Jukka, In "Sulfolane" in "The Chemistry of Nonaqueous Solvents," vol. IV, pp. 247-287, J.J. Lagowski, ed., Academic Press, 1976. Unable to Provide Full Reference.
Casteel, J.F., et al.; "Dielectric constants, viscosities, and related physical properties of 10 liquid sulfoxides and sulfones at several temperatures," J. Chem. Eng. Data, 1974, 196-200, vol. 19.

* cited by examiner

*Primary Examiner* — Liam J Heincer
*Assistant Examiner* — M. Reza Asdjodi
(74) *Attorney, Agent, or Firm* — Tristan A. Fuierer; Moore & Van Allen, PLLC; Maggie Chappuis

(57) ABSTRACT

An improved solvent containing sulfolane and at least one dialkyl sulfone, preferably dimethyl sulfone, wherein the improved solvent is a liquid at room temperature and can be used for reaction media and electrochemistry.

10 Claims, 4 Drawing Sheets

SULFOLANE MIXTURES AS AMBIENT APROTIC POLAR SOLVENTS

FIELD

The present invention relates generally to an improved solvent for reaction media and electrochemistry.

DESCRIPTION OF THE RELATED ART

Sulfolane is a well-known industrial solvent used most often for extractive distillation and to purify natural gas, and also as an aprotic reaction medium and for electrochemical applications. Advantageously, sulfolane has a high dielectric constant, a low toxicity and a very low skin penetration rate, is stable, water soluble, chemically compatible with strong acids and oxidants and bases, has a low decomposition rate, and a very high flash point. Disadvantageously, sulfolane has a high melting point of 28° C. and as such, has to be heated prior to use, or stored above its melting point, which in industrial applications requires special equipment. Moreover, the viscosity of sulfolane is high relative to many other process solvents.

Even with these disadvantages, sulfolane remains an attractive solvent. Accordingly, there is a need for a mixture comprising sulfolane that maintains or even improves on the advantages of sulfolane but minimizes or eliminates the disadvantages of sulfolane. The mixture can be used as an improved solvent for reaction media and electrochemical techniques such as lithium batteries.

SUMMARY

The present invention generally relates to an improved solvent containing sulfolane, wherein the improved solvent is a liquid at room temperature and can be used for reaction media and electrochemistry.

In one aspect, a mixture comprising sulfolane and at least one dialkyl sulfone is described, wherein the at least one dialkyl sulfone has the formula R—($SO_2$)—R', where R and R' can be the same as or different from one another and can be any $C_1$-$C_6$ alkyl group.

In another aspect, a mixture consisting of sulfolane and at least one dialkyl sulfone is described, wherein the at least one dialkyl sulfone has the formula R—($SO_2$)—R', where R and R' can be the same as or different from one another and can be any $C_1$-$C_6$ alkyl group.

In yet another aspect, a solution comprising a sulfolane mixture is described, wherein the sulfolane mixture consists of sulfolane and at least one dialkyl sulfone, wherein the at least one dialkyl sulfone has the formula R—($SO_2$)—R', where R and R' can be the same as or different from one another and can be any $C_1$-$C_6$ alkyl group, and wherein the sulfolane mixture has a melting point between about 7° C. and about 20° C.

In still another aspect, a method of lowering the melting point of sulfolane, said method comprising mixing sulfolane with at least one dialkyl sulfone, wherein the dialkyl sulfone has the formula R—($SO_2$)—R', where R and R' can be the same as or different from one another and can be any $C_1$-$C_6$ alkyl group.

In another aspect, a method of using a mixture comprising sulfolane and at least one dialkyl sulfone is described, wherein the at least one dialkyl sulfone has the formula R—($SO_2$)—R', where R and R' can be the same as or different from one another and can be any $C_1$-$C_6$ alkyl group. The mixture comprising sulfolane and at least one dialkyl sulfone can used in a reaction selected from the group consisting of silylation, aliphatic and aromatic nucleophilic substitutions, Friedel-Crafts, and electrochemical reactions.

Other aspects, features and advantages of the invention will be more fully apparent from the ensuing disclosure and appended claims.

DETAILED DESCRIPTION AND PREFERRED EMBODIMENTS THEREOF

Figure 1A:
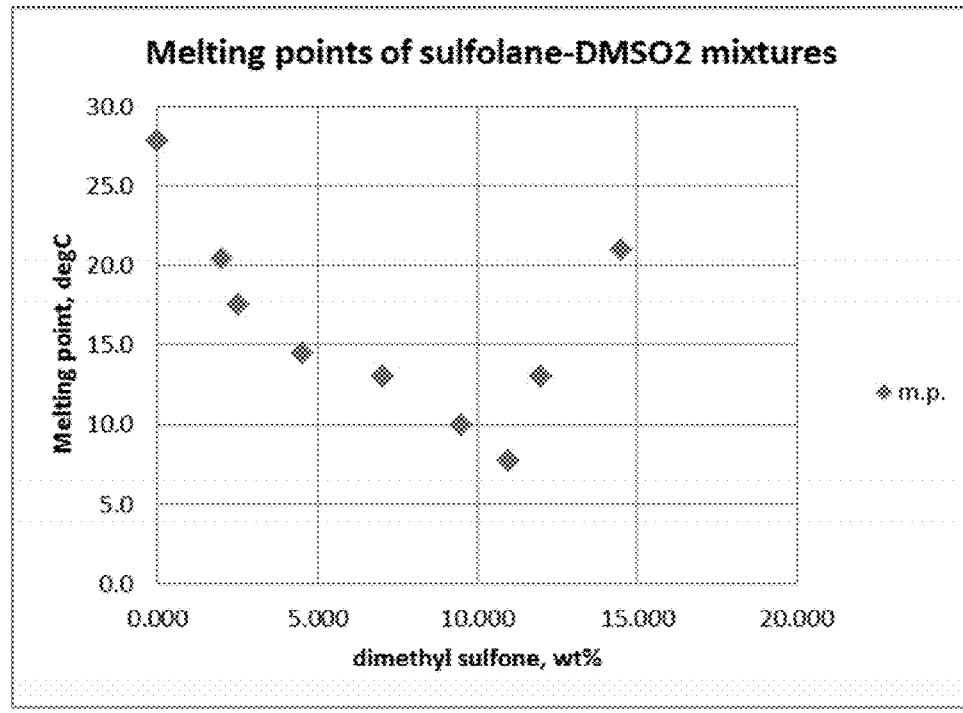
FIG. 1A illustrates the melting point of a mixture comprising sulfolane and various concentrations of dimethyl sulfone as a function of weight percent.

The present invention generally relates to relates to an improved solvent containing sulfolane, wherein the improved solvent is a liquid at room temperature and can be used for reaction media and electrochemistry.

It is well known in the chemical arts that sulfolane is synonymous with tetramethylene sulfone, tetrahydrothiophene sulfone, and tetrahydrothiophene-1,1-dioxide, and has the chemical formula $(CH_2)_4SO_2$.

Derivatives of sulfolane are defined to include compounds wherein one or more of the hydrogen atoms is replaced by an organic radical, which may contain a polar grouping and more specifically may contain oxygen, nitrogen, sulfur and/or halide atoms. Sulfolane derivatives containing oxygen include hydroxy sulfolanes, sulfolanyl-ethers and -esters; sulfolane derivatives containing nitrogen include sulfolanylamines, -nitriles and nitro sulfolanes; sulfolane derivatives containing sulfur include sulfolanyl sulfides, -sulfoxides and -sulfones. Some suitable specific sulfolane derivatives include, but are not limited to, hydrocarbon-substituted sulfolanes such as alkyl sulfolanes preferably containing not more than about 10 carbon atoms; hydroxy sulfolanes such as 3-sulfolanol, 2-sulfolanol, 3-methyl-4-sulfolanol, 3-4-sulfolanediol; sulfolanyl ethers such as methyl-3-sulfolanyl ether, propyl-3-sulfolanyl ether, allyl-3-sulfolanyl ether, butyl-3-sulfolanyl ether, crotyl-3-sulfolanyl ether, isobutyl-3-sulfolanyl ether, methallyl-3-sulfolanyl ether, methyl vinyl carbinyl-3-sulfolanyl ether, amyl-3-sulfolanyl ether, hexyl-3-sulfolanyl ether, octyl-3-sulfolanyl ether, nonyl-3-sulfolanyl ether, glycerol alpha-gamma-diallyl-beta-3-sulfolanyl ether, tetrahydrofurfuryl-3-sulfolanyl ether, 3,3,5-tetramethyl-cyclohexyl-3-sulfolanyl ether, m-cresyl-3-sulfolanyl ethers, corresponding 2-sulfolanyl ethers, disulfolanyl ethers; sulfolanyl esters such as 3-sulfolanyl actetate, 3-sulfolanylcaproate, sulfolanyllaurate, sulfolanylpalmitate, sulfolanylstearate, sulfolanyloleate, sulfolanylpropionate, sulfolanylbutyrate; N-sulfolanes such as 3-sulfolanylamine, N-methyl-3-sulfolanylamine, N-ethyl-3-sulfolanylamine, N—N-dimethyl-3-sulfolanylamine, N-allyl-3-sulfolanylamine, N-butyl-3-sulfolanylamine, N-octyl-3-sulfolanylamine; sulfolanyl sulfides such as ethyl- 3tertiary butyl-3-sulfolanyl sulfide, isobutyl-3-sulfolanyl sulfide, methallyl-3-sulfolanyl sulfide, di-3-sulfolanyl sulfide; sulfolanyl sulfones such as methyl-3-sulfolanyl sulfone, ethyl-3-sulfolanyl sulfone, propyl-3-sulfolanyl sulfone, amyl-3-sulfolanyl sulfone; and sulfolanyl halides such as 3-chloro-sulfolanyl halide, 3-4-dichloro-sulfolanyl halide, 3-chloro-4-methyl sulfolanes.

"Substantially devoid" is defined herein as less than 2 wt. %, preferably less than 1 wt. %, more preferably less than 0.5 wt. %, even more preferably less than 0.1 wt. %, and most preferably 0 wt %.

Disadvantageously, sulfolane has a melting point of approximately 2.8° C. which means that for processes at ambient temperature, sulfolane must be melted or kept warm, which is inconvenient. That said, sulfolane has a very high cryoscopic constant (approximately 64-66 K·kg/mole) and as such, the addition of a soluble additive to sulfolane should lower the melting point to 20° C. or below. For example, it is known that water can be added to sulfolane and the melting point lowered to 0° C. (see, Tilstam, U., *Org. Process Res. Dev.*, 2012, 16, 1273-1278). Unfortunately, many reactions and electrochemical techniques must be carried out in the absence of water. Accordingly, additives must be determined which have properties similar to sulfolane, are inexpensive, and are non-toxic such that a mixture of sulfolane and the additive(s) are a suitable replacement for pure sulfolane.

It was discovered by the present inventor that a mixture comprising sulfolane and at least one dialkyl sulfone lowers the melting point of sulfolane to a range below room temperature, while maintaining the multiple advantages of 100% sulfolane. Advantages include, but are not limited to: an essentially unchanged chemical behavior, which is not possible when water is added to sulfolane; maintaining a very high boiling point and flash point, which is especially important when reactions must be performed at high temperatures; lowering rather than increasing viscosity, and using an additive that is widely available, cost effective, and of low or no toxicity.

Dialkyl sulfones contemplated have the formula R—(SO$_2$)—R', where R and R' can be the same as or different from one another and can be any $C_1$-$C_6$ alkyl group, including dimethylsulfone (also called methyl sulfonyl methane, MSM, DMSO$_2$), ethyl methyl sulfone, dipropyl sulfone, ethyl propyl sulfone, diethyl sulfone, dibutyl sulfone, and combinations thereof.

Preferably, the at least one dialkyl sulfone comprises dimethyl sulfone. Dimethyl sulfone has solvent properties similar to sulfolane, but also advantageously has a high boiling point, high flash point, no known toxicity, and is highly stable. At 125° C., where both compounds are liquid and can be compared directly, dimethyl sulfone actually has a significantly higher dielectric constant (45.00 vs. 32.74 for sulfolane) and lower viscosity (1.14 cP vs. 1.835 cP for sulfolane), see J. F. Casteel and P. G. Sears, J. Chem. Eng. Data 19 (3), 196 (1974). The higher dielectric constant and lower viscosity both tend to increase the maximum achievable conductivity of dissolved salts, by increasing salt solubility, decreasing the extent of ion pairing, and increasing the equivalent conductance because of the higher diffusion coefficients of ions in a lower viscosity medium. These factors serve to make the proposed mixtures more useful than sulfolane itself for applications such as batteries and supercapacitors. Surprisingly, even though dimethyl sulfone has a melting point of 109° C. and sulfolane has a melting point between 28.4-28.8° C., a solution that is 2.5 wt % dimethyl sulfone in sulfolane had a melting point of 17.5° C.

Accordingly, in one aspect of the invention, a solvent mixture comprising, consisting of, or consisting essentially of sulfolane and at least one dialkyl sulfone is described. In one embodiment, the solvent mixure comprising, consisting of, or consisting essentially of sulfolane and at least one dialkyl sulfone is substantially devoid of water. In another embodiment, the solvent mixure comprising, consisting of, or consisting essentially of sulfolane and at least one dialkyl sulfone is devoid of water. In yet another embodiment, the solvent mixture comprising, consisting of, or consisting essentially of sulfolane and at least one dialkyl sulfone has a melting point between about 10° C. and about 20° C., and is preferably a liquid at room temperature (e.g., 20° C.). In still another embodiment, the solvent mixture comprising, consisting of, or consisting essentially of sulfolane and at least one dialkyl sulfone is substantially devoid of water and has a melting point between about 10° C. and about 20° C., and is preferably a liquid at room temperature. In a particularly preferred embodiment, the solvent mixture comprises or consists of sulfolane and dimethyl sulfone and is substantially devoid of water.

The amounts of sulfolane and at least one dialkyl sulfone can be determined by the person skilled in the art and preferably is in the range of 1 wt %-15 wt % dialkyl sulfone and 85 wt % to 99 wt % sulfolane. The resulting solvent mixture (i) has a higher dielectric constant than pure sulfolane, which can increase reaction rates, (ii) has a lower viscosity than pure sulfolane, and can be used for electrochemical uses such as Li batteries.

In one embodiment, the solvent mixture comprises approximately 2.5-4 mole % dialkyl sulfone, which is advantageous if the intention is to have a liquid that is storable and pumpable at room temperature, but with properties practically indistinguishable from sulfolane.

In another embodiment, the solvent mixture comprises approximately 13-14 mole % dialkyl sulfone, which is advantageous if the intention is to have a liquid that is maximally ensured not to freeze during transit or cool storage conditions. Advantageously, for solvent mixtures containing >11 wt % dimethyl sulfone, the bulk doesn't freeze when the temperature drops below the liquidus temperature. There may be a small amount of dimethyl sulfone particles forming, but the bulk of the mixture is still liquid and fluidic. Therefore, if a 14-15 wt % dimethyl sulfone mixture is allowed to cool down below its liquidus temperature, it is a simple matter to redissolve the precipitated dimethyl sulfone by pumping the mostly liquid mixture through a heat exchanger. This is not possible with pure sulfolane, which needs to be kept in special heated storage tanks and pumped through warmed-up piping and valves.

In still another embodiment, the solvent mixture comprises approximately 14-15 wt % dialkyl sulfone, which is advantageous if the intention is to get the maximum improvement in terms of a higher polarity and/or lower viscosity fully liquid solvent.

Higher amounts of dialkyl sulfone in the solvent mixture are contemplated. For example, if one wants to keep the heated storage and pumping system but benefit from the lower viscosity and higher polarity of sulfolane-dimethyl sulfone mixtures, one can use even higher dimethyl sulfone contents (approximately 20-50 wt % or even higher with 50-80 wt % sulfolane) by relying on the "non-frozen bulk" property of the high dimethyl sulfone mixtures, essentially storing a slurry of dimethyl sulfone in sulfolane, preferably in continuous circulation so the dimethyl sulfone doesn't sink and compact itself on the bottom, and heating it further up to usage temperature to melt all the dimethyl sulfone when needed. For example, a mixture containing 58% sulfolane and 42% dimethyl sulfone—in which the dimethyl sulfone is partially dissolved but mostly suspended at room temperature—forms an easily manageable slurry (stirrable and pipettable) at room temperature. When heated to 70° C. it becomes completely liquid, but when cooled down slowly with stirring back to room temperature it returns to a fluid slurry state. A sample of the aforementioned slurry was still a fluid one year after the initial preparation.

In another aspect, a method of lowering the melting point of sulfolane is described, said method comprising mixing sulfolane with at least one dialkyl sulfone, wherein the dialkyl sulfone has the formula R—($SO_2$)—R', where R and R' can be the same as or different from one another and can be any $C_1$-$C_6$ alkyl group.

In another aspect, the solvent mixture is used in place of pure sulfolane for reactions such as silylation, aliphatic and aromatic nucleophilic substitutions, Friedel-Crafts, and for electrochemical reactions.

In still another aspect, the solvent mixture is used in place of pure sulfolane in extraction processes. The solubility of a typical low-polarity solvent (methyl tert-butyl ether, MTBE) is approximately 15% lower in 14.5 wt % dimethyl sulfone/85.5 wt % sulfolane than in pure sulfolane. This makes work-up of reaction mixtures more efficient when lower-polarity products are best separated by extraction, e.g., facilitating the reuse of the solvent after evaporation of the residual MTBE and/or avoiding the need to add water to the solvent.

In another aspect, a solution comprising a sulfolane mixture is described, wherein the sulfolane mixture consists of sulfolane and at least one dialkyl sulfone, wherein the at least one dialkyl sulfone has the formula R—($SO_2$)—R', where R and R' can be the same as or different from one another and can be any $C_1$-$C_6$ alkyl group, and wherein the sulfolane mixture has a melting point between about 7° C. and about 20° C.

In yet another aspect, a method of preserving and using a mixture of sulfolane and up to about 50% dimethyl sulfone in fluid state is described, whereby the mixture is kept as a slurry, preferably stirred and/or circulated, at or near room temperature, and is used as an essentially homogeneous liquid serving as reaction medium or electrochemical medium at higher temperatures.

The features and advantages of the invention are more fully illustrated by the following non-limiting examples, wherein all parts and percentages are by weight, unless otherwise expressly stated.

EXAMPLE 1

Figure 1B:
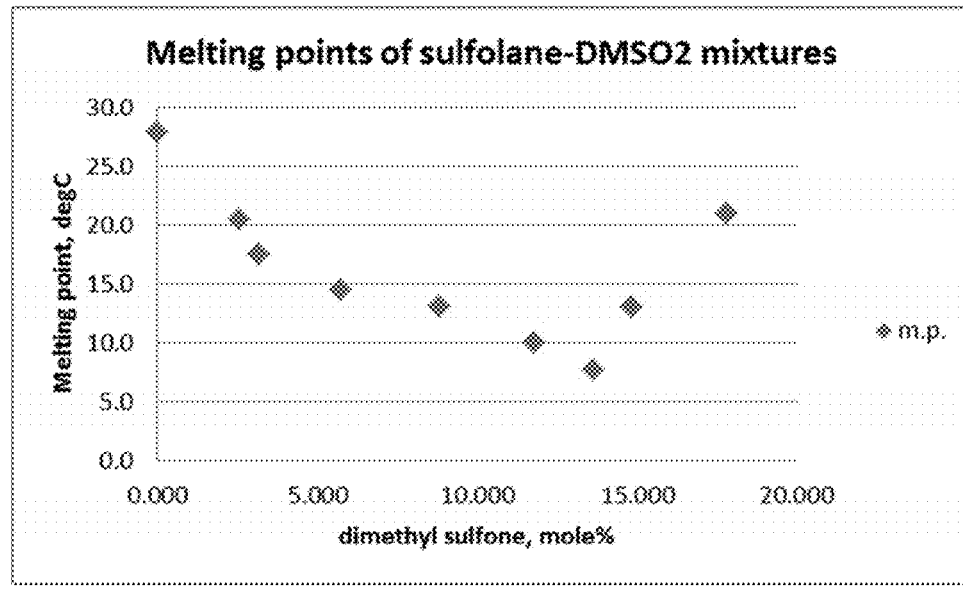
FIG. 1B illustrates the melting point of a mixture comprising sulfolane and various concentrations of dimethyl sulfone as a function of mole percent.

Mixtures of sulfolane with various concentrations of dimethyl sulfone were prepared and the melting point determined. Referring to FIGS. 1A and 1B, the eutectic point can be visually identified.

EXAMPLE 2

Mixtures of sulfolane with various concentrations of dimethyl sulfone (0, 2.5 wt %, 11 wt % and 14.5 wt %) were prepared and the density and viscosity determined. Density of the mixtures was measured at 22.1° C. and extrapolated to 21 and 30° C., assuming a temperature coefficient of −0.00085 g/(cc·deg). The density of pure sulfolane at 30° C., taken from the literature, is an average of seven quoted values ranging from 1.2626 to 1.2614 g/cc. Sulfolane density and the density temperature coefficient are based on data compiled by Jukka Martinmaa in "Sulfolane," in "The Chemistry of Nonaqueous Solvents," vol. IV, pp. 247-287, J. J. Lagowski, ed., Academic Press, 1976. The density results are shown in Table 1 below:

| Sample # | wt % dimethyl sulfone | density (21° C.) | density (30° C.) |
|---|---|---|---|
| 1 | 0 | | 1.262 |
| 2 | 2.5 | 1.269 | 1.261 |
| 3 | 11 | 1.266 | 1.259 |
| 4 | 14.5 | 1.265 | 1.257 |

Figure 2:
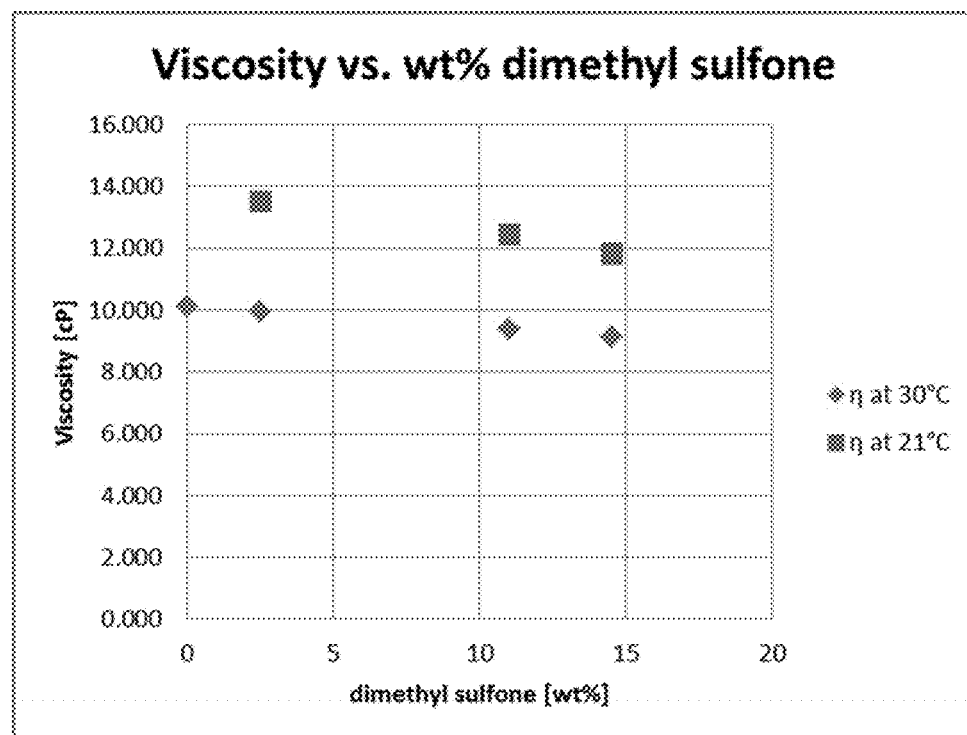
FIG. 2 illustrates the viscosity of the mixture as a function of wt % of dimethyl sulfone.

The dynamic viscosity data are derived from experimental kinematic viscosity data by multiplication by the density. The viscosity as a function of wt % of dimethyl sulfone is shown in FIG. 2, where it can be seen that the addition of 14.5% dimethyl sulfone to sulfolane lowers the viscosity approximately 10% or more.

EXAMPLE 3

Figure 3:
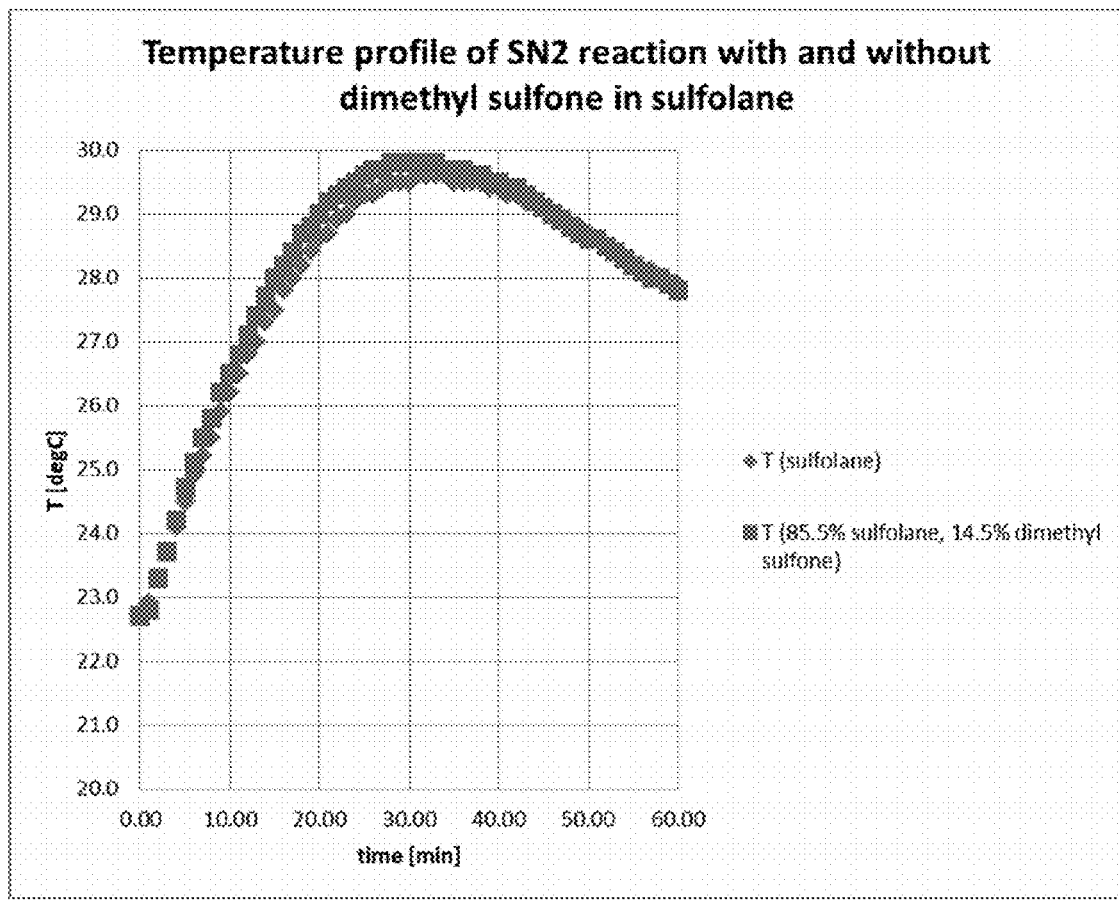
FIG. 3 illustrates the temperature profile of a fast $S_N2$ reaction that proceeds through a charged activated complex.

FIG. 3 illustrates the temperature profile of a fast $S_N2$ reaction that proceeds through a charged activated complex and as such is facilitated by a higher dielectric constant of an aprotic solvent. The reaction was between N-methylimidazole (0.515 g, 6.27 mmol) and diethyl sulfate (0.942 g, 6.11 mmol) in 9 g of solvent mixture (100% sulfolane vs. 85.5% sulfolane-14.5% dimethyl sulfone). The higher dT/dt slope and the earlier time at which the maximum temperature is reached show that higher concentrations of dimethyl sulfone speed up the reaction somewhat.

Figure 4:
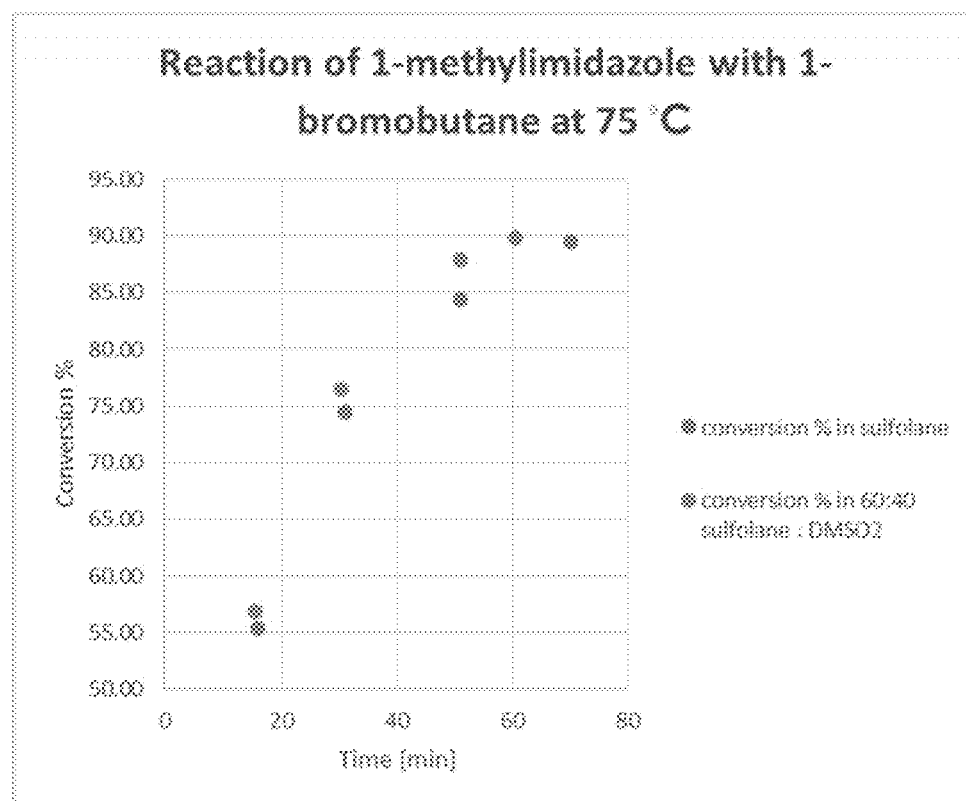
FIG. 4 illustrates the conversion of reactant to product as a function of time that is facilitated by a higher dielectric constant by incorporating a high concentration of dimethyl sulfone in sulfolane.

FIG. 4 illustrates the conversion of reactant to product as a function of time in a slower $S_N2$ reaction that is facilitated by a higher dielectric constant by incorporating a high concentration of dimethyl sulfone in sulfolane. Here the solvent was either pure sulfolane, or a mixture of 60% sulfolane and 40% dimethyl sulfone, which is a fluid slurry at room temperature. The reaction was between N-methylimidazole (1.23 g, 15 mmol) and 2.32 g 1-bromobutane (16.9 mmol) in 10 g of solvent. The reaction was performed in NMR tubes and monitored by proton NMR at 75° C., with the bromobutane added last to a mixture of the solvent and N-methylimidazole. As the reaction proceeded, the three neutral aromatic imidazole proton peaks and the aliphatic protons in alpha positions to the nitrogen atoms were replaced by the corresponding downfield-shifted peaks of the imidazolium ion protons, enabling easy in-situ quantification of the respective concentrations. It can be seen that the reaction is slightly faster in the mixed solvent than in pure sulfolane.

Although the invention has been variously disclosed herein with reference to illustrative embodiments and features, it will be appreciated that the embodiments and features described hereinabove are not intended to limit the invention, and that other variations, modifications and other embodiments will suggest themselves to those of ordinary skill in the art, based on the disclosure herein. The invention therefore is to be broadly construed, as encompassing all such variations, modifications and alternative embodiments within the spirit and scope of the claims hereafter set forth.

What is claimed is:

1. A mixture consisting of 85 wt % to 99 wt % of sulfolane and 1 wt %-15 wt % of at least one dialkyl sulfone, wherein the at least one dialkyl sulfone has the formula R—($SO_2$)—R', where R and R' can be the same as or different from one another and can be any $C_1$-$C_6$ alkyl group.

2. The mixture of claim 1, wherein the at least one dialkyl sulfone is selected from the group consisting of dimethylsulfone, ethyl methyl sulfone, dipropyl sulfone, ethyl propyl sulfone, diethyl sulfone, dibutyl sulfone, and combinations thereof.

3. The mixture of claim 1, wherein the at least one dialkyl sulfone comprises dimethylsulfone.

4. The mixture of claim 1, wherein the mixture is substantially devoid of water.

5. The mixture of claim 1, wherein the mixture has a melting point between about 7° C. and about 20° C.

6. The mixture of claim 1, wherein the mixture is a liquid at room temperature.

7. A method of lowering the melting point of sulfolane, said method comprising preparing a mixture consisting of 85 wt % to 99 wt % of sulfolane and 1 wt %-15 wt % of at least one dialkyl sulfone, wherein the dialkyl sulfone has the formula R—(SO$_2$)—R', where R and R' can be the same as or different from one another and can be any $C_1$-$C_6$ alkyl group.

8. The method of claim 7, wherein the mixture of sulfolane and at least one dialkyl sulfone is substantially devoid of water.

9. The method of claim 7, wherein the mixture of sulfolane and at least one dialkyl sulfone has a melting point between about 7° C. and about 20° C.

10. The method of claim 7, wherein the at least one dialkyl sulfone is selected from the group consisting of dimethylsulfone, ethyl methyl sulfone, dipropyl sulfone, ethyl propyl sulfone, diethyl sulfone, dibutyl sulfone, and combinations thereof.

\* \* \* \* \*